US011107563B2

(12) United States Patent
Vogt et al.

(10) Patent No.: US 11,107,563 B2
(45) Date of Patent: Aug. 31, 2021

(54) FAST HEALTHCARE INTEROPERABILITY RESOURCES MODEL FOR USER INTERFACE GENERATION

(71) Applicant: SAP SE, Walldorf (DE)

(72) Inventors: Florian Vogt, Bad Schoenborn (DE); Jan-Philip Zieher, Mannheim (DE); Oliver Grande, Heidelberg (DE); Thomas Kanthak, Heidelberg (DE)

(73) Assignee: SAP SE, Walldorf (DE)

( * ) Notice: Subject to any disclaimer, the term of this patent is extended or adjusted under 35 U.S.C. 154(b) by 324 days.

(21) Appl. No.: 16/264,940

(22) Filed: Feb. 1, 2019

(65) Prior Publication Data
US 2020/0251194 A1 Aug. 6, 2020

(51) Int. Cl.
*G16H 10/60* (2018.01)
*G16H 15/00* (2018.01)
*G06F 16/81* (2019.01)

(52) U.S. Cl.
CPC ............ *G16H 10/60* (2018.01); *G06F 16/81* (2019.01); *G16H 15/00* (2018.01)

(58) Field of Classification Search
CPC ........ G16H 10/60; G16H 15/00; G16H 80/00; G06F 16/81
See application file for complete search history.

(56) References Cited

U.S. PATENT DOCUMENTS

| 2016/0203281 A1* | 7/2016 | Zalis | G16H 10/60 |
| | | | 705/3 |
| 2017/0270532 A1* | 9/2017 | Livesay | G06Q 30/01 |
| 2018/0181716 A1* | 6/2018 | Mander | G06Q 10/0633 |
| 2020/0143913 A1* | 5/2020 | Castine | G16H 10/60 |

FOREIGN PATENT DOCUMENTS

CA 2661928 A1 * 5/2008 ............. G16H 10/60

OTHER PUBLICATIONS

Kasthurirathne, Suranga N; et al. "Enabling Better Interoperability for Healthcare: Lessons in Developing a Standards Based Application Programing Interface for Electronic Medical Record Systems." Journal of Medical Systems 39. 11 SPRINGER (Nov. 2015) (Year: 2015).*

* cited by examiner

*Primary Examiner* — Linh Giang Le
(74) *Attorney, Agent, or Firm* — Schwegman Lundberg & Woessner, P.A.

(57) ABSTRACT

An application file defines a first data object that identifies a fast healthcare interoperability resources (FHIR) server and a second data object that identifies a data type associated with the FHIR server. Based on the first data object and the second data object, a FHIR model requests data of the data type from the FHIR server. The FHIR server provides the requested data, which is received by the FHIR model. Based on the received data, the FHIR model generates data in a user interface (UI) control format and provides the generated data to a UI module that causes a UI to be presented. The FHIR model supports binding of complete entities such as patients or organizations to a UI. This binding enables the requesting of whole entities from a FHIR endpoint, provision of the entity data to the UI, and updating the FHIR data.

20 Claims, 15 Drawing Sheets

|  | PATIENT TABLE 410 | | |
|---|---|---|---|
| PATIENT ID (420) | NAME | BIRTHDATE | INSURANCE |
| 1 (430A) | HOWARD, MOSES | 1897-06-19 | NONE |
| 2 (430B) | LIVINGSTON, ANNA | 1983-02-17 | KAISER FOUNDATION |
| 3 (430C) | MADDEN, TOBI | 1983-02-17 | NONE |
| 123 (430D) | SHMOE, JOE | 1983-04-01 | UNITED HEALTH |

*FIG. 4*

```
                                    ┌─510
"APP": {
   "DATASOURCES": {
      "MYFHIRSERVICE": {
         "URI": "HTTPS://MYFHIRSERVICEHOST.COM/FHIR/",
         "TYPE": "FHIR"
      }
   }
},
"UI": {
   "FHIRMODEL": {
      "TYPE": "FHIRMODEL",
      "DATASOURCE": "MYFHIRSERVICE"
   }
}
```

```
                                    ┌─520
<PAGE ID="MYPAGE" BINDING="{/PATIENT/123}">
      <TEXT TEXT="{NAME}" />
      <TEXT TEXT="{BIRTHDATE}" />
      <PANEL BINDING="{ANIMAL}">
      </PANEL>
</PAGE>

FUNCTION ONINPUTCHANGE(OEVENT){
      VAR SVALUE = OEVENT.GETPARAMETER("VALUE");
      THIS.BYID("MYPAGE").BINDELEMENT("/PATIENT/" + SVALUE);
}
```

*FIG. 5*

```html
<!DOCTYPE HTML>
<HTML>
  <HEAD>
    <META HTTP-EQUIV="X-UA-COMPATIBLE" CONTENT="IE=EDGE" />
    <META CHARSET="UTF-8">
    <TITLE>MYHEALTHAPP</TITLE>
    <SCRIPT ID="UI-BOOTSTRAP" SRC="HTTPS://UI.ONDEMAND.COM/RESOURCES/UI-CORE.JS"
        DATA-UI-LIBS="M"
        DATA-UI-THEME="BELIZE"
        DATA-UI-COMPATVERSION="EDGE" DATA-UI-PRELOAD="ASYNC"
        DATA-UI-RESOURCEROOTS='{"MYHEALTHAPP": ""}'>
    </SCRIPT>
    <LINK REL="STYLESHEET" TYPE="TEXT/CSS" HREF="CSS/STYLE.CSS">
    <SCRIPT>
      UI.GETCORE().ATTACHINIT(FUNCTION() {
        NEW M.SHELL({
          APP: NEW UI.CORE.COMPONENTCONTAINER("HEALTHCOMPONENTCONTAINER",{
            HEIGHT : "100%",
            NAME : "MYHEALTHAPP",
            SETTINGS : {
              ID : "HEALTHCOMPONENT"
            }
          })
        }).PLACEAT("CONTENT");
      });
    </SCRIPT>
  </HEAD>
  <BODY CLASS="UIBODY" ID="CONTENT">
  </BODY>
</HTML>
```

*FIG. 6*

```
UI.DEFINE(["UI/CORE/UICOMPONENT"], FUNCTION(UICOMPONENT) {
  "USE STRICT";

RETURN UICOMPONENT.EXTEND("MYHEALTHAPP.COMPONENT", {

METADATA: {
      MANIFEST: "JSON"
    },

INIT: FUNCTION() {
      UICOMPONENT.PROTOTYPE.INIT.APPLY(THIS, ARGUMENTS);
      THIS.GETROUTER().INITIALIZE();
    }
  });
});
```

FIG. 7

```xml
<CORE:VIEW XMLNS:CORE="I.CORE" XMLNS:MVC="UI.CORE.MVC"
XMLNS="M" CONTROLLERNAME="MYHEALTHAPP.CONTROLLER.HOME"
  XMLNS:HTML="HTTP://WWW.W3.ORG/1999/XHTML">
    <PAGE TITLE="{I18N>TITLE}">
      <CONTENT>
        <GENERICTILE ID="MYPATIENTSTILE"
CLASS="UITINYMARGINBEGIN UITINYMARGINTOP" HEADER="MY
PATIENTS" PRESS="ONMYPATIENTSTILEPRESS">
          <TILECONTENT UNIT="PATIENTS">
            <NUMERICCONTENT VALUE="125" ICON="ICON://
STETHOSCOPE"/>
          </TILECONTENT>
        </GENERICTILE>
        <GENERICTILE ID="MYORGANIZATIONSTILE"
CLASS="UITINYMARGINBEGIN UITINYMARGINTOP" HEADER="MY
ORGANIZATIONS" PRESS="ONMYORGANZATIONSTILEPRESS">
          <TILECONTENT UNIT="ORGANIZATIONS">
            <NUMERICCONTENT VALUE="3" ICON="ICON://ORG-CHART"/
>
          </TILECONTENT>
        </GENERICTILE>
      </CONTENT>
    </PAGE>
</CORE:VIEW>
```

*FIG. 8*

```
UI.DEFINE([
    "UI/CORE/MVC/CONTROLLER"
], FUNCTION(CONTROLLER) {
    "USE STRICT";

RETURN CONTROLLER.EXTEND("MYHEALTHAPP.CONTROLLER.HOME",
{

ONMYPATIENTSTILEPRESS: FUNCTION(OEVENT) {

M.MESSAGETOAST.SHOW(THIS.GETVIEW().GETMODEL("I18N").GETRESOURCEBUNDLE().GETTEXT("PATIENTSTILEINFO", "125"))
        },

ONMYORGANZATIONSTILEPRESS: FUNCTION(OEVENT) {

M.MESSAGETOAST.SHOW(THIS.GETVIEW().GETMODEL("I18N").GETRESOURCEBUNDLE().GETTEXT("ORGANZATIONSTILEINFO", "3"))
        }
    });
});
```

FIG. 9

```
{
 "WELCOMEFILE": "/MYHEALTHAPP/INDEX.HTML",
 "AUTHENTICATIONMETHOD": "NONE",
 "ROUTES": [{
      "SOURCE": "^/MYHEALTHAPP/RESOURCES/HEALTH/MODEL/FHIR/(.*)$",
      "TARGET": "$1",
      "LOCALDIR": "../NODE_MODULES/FHIR-UI-MODEL/SRC/HEALTH/MODEL/FHIR"
   }, {
      "SOURCE": "^/MYHEALTHAPP/(.*)$",
      "TARGET": "$1",
      "LOCALDIR": "../WEBAPP"
   }, {
      "SOURCE": "^/R4/(.*)$",
      "TARGET": "/R4/$1",
      "DESTINATION": "FHIRBACKEND",
      "CSRFPROTECTION": FALSE
   }
 ]
}
```

*FIG. 10*

```
                       ┌─ 1110
"DATASOURCES": {
  "FHIR": {
    "URI": "/R4",
    "TYPE": "FHIR"
  }
}
```

```
                   ┌─ 1120
"RESOURCEROOTS": {
  "HEALTH.MODEL.FHIR": "RESOURCES/HEALTH/MODEL/FHIR/"
}
```

```
         ┌─ 1130
"": {
  "TYPE": "HEALTH.MODEL.FHIR.FHIRMODEL",
  "DATASOURCE": "FHIR"
}
```

*FIG. 11*

```
<CORE:VIEW XMLNS:CORE="UI.CORE" XMLNS:MVC="UI.CORE.MVC"
XMLNS="M" CONTROLLERNAME="MYHEALTHAPP.CONTROLLER.HOME"
XMLNS:HTML="HTTP://WWW.W3.ORG/1999/XHTML">
   <PAGE TITLE="{I18N>TITLE}">
     <CONTENT>
       <GENERICTILE ID="MYPATIENTSTILE" BINDING="{/PATIENT}"
CLASS="UITINYMARGINBEGIN UITINYMARGINTOP" HEADER="MY
PATIENTS" PRESS="ONMYPATIENTSTILEPRESS">
         <TILECONTENT UNIT="PATIENTS">
           <NUMERICCONTENT VALUE="{%TOTAL%}" ICON="ICON://
STETHOSCOPE"/>
         </TILECONTENT>
       </GENERICTILE>
       <GENERICTILE ID="MYORGANIZATIONSTILE" BINDING="{/
ORGANIZATION}" CLASS="UITINYMARGINBEGIN UITINYMARGINTOP"
HEADER="MY ORGANIZATIONS"
PRESS="ONMYORGANZATIONSTILEPRESS">
         <TILECONTENT UNIT="ORGANIZATIONS">
           <NUMERICCONTENT VALUE="{%TOTAL%}" ICON="ICON://ORG-
CHART"/>
         </TILECONTENT>
       </GENERICTILE>
     </CONTENT>
     <FOOTER>
       <TOOLBAR>
         <LABEL TEXT="{I18N>HOMEFOOTERTEXT}"/>
       </TOOLBAR>
     </FOOTER>
   </PAGE>
</CORE:VIEW>
```

*FIG. 12*

```
                                    ┌─1300
                                   ╱
┌─────────────────────────────────────────────────────────┐
│                                                  _ □ X  │
│               ┌─PATIENT SEARCH─┐ ~1310                   │
│  ┌DATE OF BIRTH:┐~1320  ┌NAME:┐~1330  ┌INSURANCE PROVIDER:┐~1340
│  │ FEB. 17, 1983│~1350  │     │~1360  │      ALL       ▼│~1370
│                              ~1380
│  ┌──────────────────────────────────────────────────┐   │
│  │ NAME           DATE OF BIRTH   INSURANCE PROVIDER│   │
│  │                                                  │   │
│  │ LIVINGSTON, ANNA  FEB. 17, 1983  KAISER FOUNDATION│  │
│  │ MADDEN, TOBI      FEB. 17, 1983  NONE            │   │
│  │ MILES, JESSE      FEB. 17, 1983  UNITED HEALTH   │   │
│  │ MILLER, MAYA      FEB. 17, 1983  HCSC GROUP      │   │
│  │ NELSON, JULIE     FEB. 17, 1983  UNITED HEALTH   │   │
│  │ PERSON, ISAAC     FEB. 17, 1983  NONE            │   │
│  │ WALTERS, SEAN     FEB. 17, 1983  HCSC GROUP      │   │
│  │ WINTER, MARVIN    FEB. 17, 1983  KAISER FOUNDATION│  │
│  └──────────────────────────────────────────────────┘   │
└─────────────────────────────────────────────────────────┘
```

*FIG. 13*

FAST HEALTHCARE INTEROPERABILITY RESOURCES MODEL FOR USER INTERFACE GENERATION

TECHNICAL FIELD

The subject matter disclosed herein generally relates to user interfaces. Specifically, the present disclosure addresses systems and methods to generate user interfaces from fast healthcare interoperability resources (FHIR) data.

BACKGROUND

User interface (UI) platforms can create user interfaces using Open Data Protocol (OData). A user interface definition specifies one or more OData services and, based on the specified services, the UI platform creates a user interface to view or modify data provided by the services.

FHIR is a standard for health care data exchange. The FHIR specification uses representational state transfer (REST) techniques to enable integration of a wide range of healthcare teams and organizations. FHIR is based on resources, each of which is defined by a uniform resource locator (URL), metadata, a set of defined data elements, and an extensibility framework.

Healthcare data is generated by doctors, hospitals, patients, and insurance companies, and is stored is an electronic health record (EMR). FHIR standardizes the format of the healthcare records and allows for data interchange between the diverse entities that create, modify, and use healthcare data. The structure of FHIR structure definitions is stored in a FHIR structure definition, so FHIR is self-descriptive.

BRIEF DESCRIPTION OF THE DRAWINGS

Some embodiments are illustrated by way of example and not limitation in the figures of the accompanying drawings.

FIG. 4 is a block diagram of a database schema suitable for storing FHIR data, according to some example embodiments.

FIG. 5 is an example of portions of configuration files for a UI application suitable for using a FHIR model.

FIG. 6 is an example of a hypertext markup language (HTML) file suitable for providing a UI application using a FHIR model.

FIG. 7 is an example of portions of configuration files for a UI application suitable for using a FHIR model.

FIG. 8 is an example of an extensible markup language (XML) file suitable for providing a view of a UI application using a FHIR model.

FIG. 9 is an example of a configuration file suitable for providing a controller of a UI application using a FHIR model.

FIG. 10 is an example of a configuration file suitable for configuring an application router for use with a UI application using a FHIR model.

FIG. 11 is an example of portions of a manifest file for a UI application suitable for using a FHIR model.

FIG. 12 is an example of an XML file suitable for providing a view of a UI application using a FHIR model.

FIG. 13 is a block diagram of an example user interface generated using a FHIR model.

DETAILED DESCRIPTION

Figure 1:
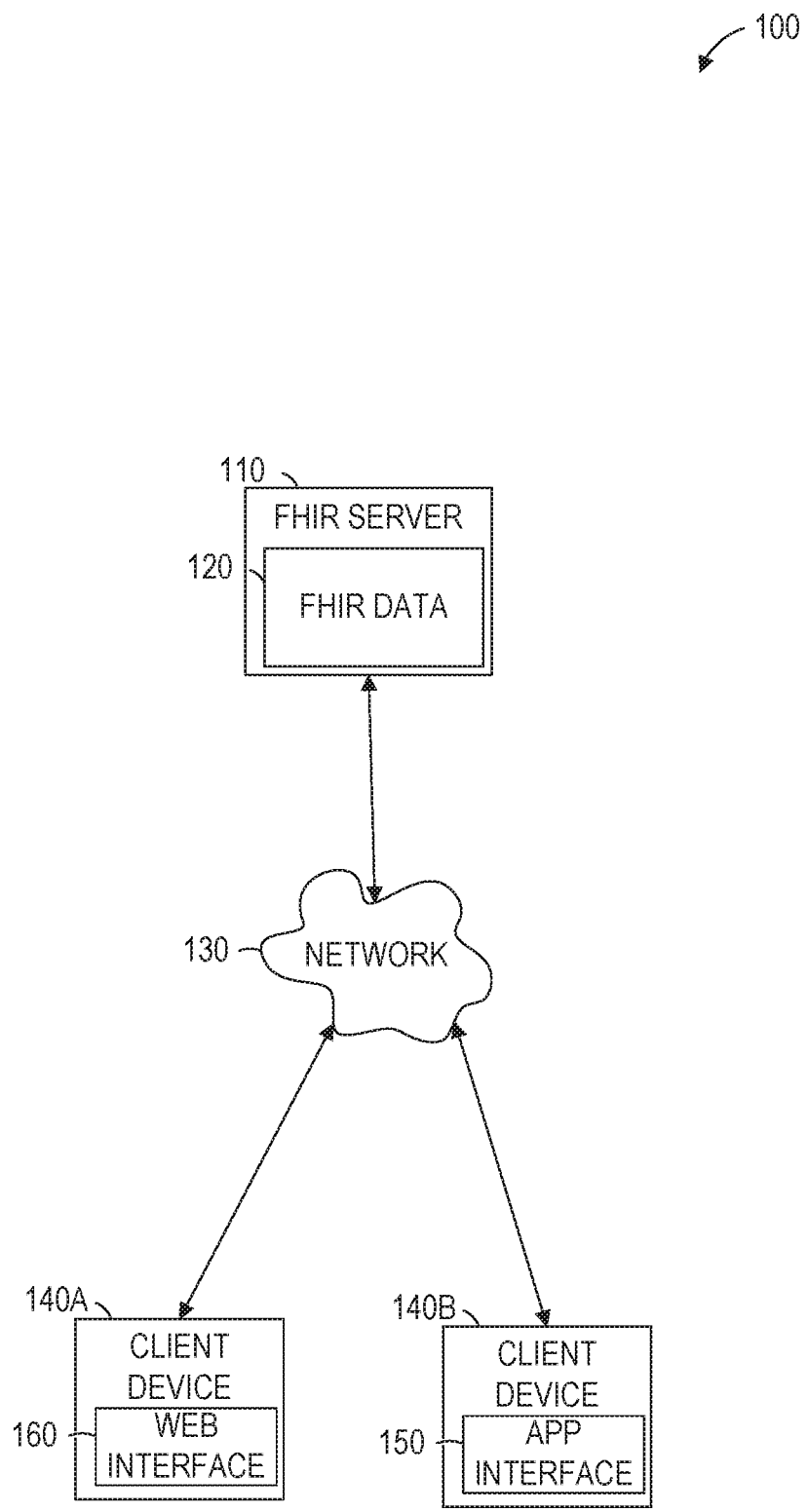
FIG. 1 is a network diagram illustrating a network environment suitable for using a FHIR model, according to some example embodiments.

Methods and systems described herein are directed to using a FHIR model to generate user interfaces. An application file defines a first data object that identifies a FHIR server and a second data object that identifies a data type associated with the FHIR server. Based on the first data object and the second data object, the FHIR model requests data of the data type from the FHIR server. The FHIR server provides the requested data, which is received by the FHIR model. Based on the received data, the FHIR model generates data in a UI control format and provides the generated data to a UI module that causes a UI to be presented.

The FHIR model supports binding of complete entities such as patients or organizations to a UI. This binding, referred to as context binding, enables the requesting of whole entities from a FHIR endpoint and provision of the entity data to the UI.

The FHIR model also supports binding of single properties of a FHIR resource. Data retrieved by the FHIR model during the context binding is provided from the FHIR model to a single UI control without making another request to the FHIR endpoint.

Data for multiple resources can be requested for inclusion in a UI. For example, a list of patients may be displayed in a table. This is handled using list binding. The FHIR model requests data for the multiple resources from the FHIR endpoint and binds the resulting data into a list for use by the UI.

While FHIR does not provide tree structured data innately, the FHIR model is able to generate a tree structure from FHIR data using tree binding. For example, a UI may display a tree of organizations with a company at the root, each hospital as a first level branch, the wards within the hospital as the second level branches, and so on. The FHIR model receives flat data from the FHIR endpoint and binds the received data into a tree structure for use by the UI.

To reduce the number of requests to the FHIR endpoint, the FHIR model supports bundled requests. When requests are bundled, data for multiple entities is requested from the FHIR endpoint in a single request. Requests are bundled as either a batch or a transaction. When processed as a batch, each request is independently handled. When processed as a transaction, if any request fails, the entire bundle is not performed at all.

By comparison with existing methods of generating FHIR UIs, the methods and systems discussed enable application developers to create UI applications based on a FHIR endpoint more easily than was previously possible. The reusable FHIR model can be effectively optimized to a greater degree due to its reusability. When these effects are considered in aggregate, one or more of the methodologies described herein may obviate a need for certain efforts or resources that otherwise would be involved in generating FHIR UIs. Computing resources used by one or more machines, databases, or networks may similarly be reduced. Examples of such computing resources include processor cycles, network traffic, memory usage, data storage capacity, power consumption, and cooling capacity.

FIG. 1 is a network diagram illustrating a network environment suitable for using a FHIR model, according to some example embodiments. The network environment 100 includes a FHIR server 110 with FHIR data 120, client devices 140A and 140B, and a network 130. The FHIR server 110 provides FHIR data 120 to the client devices 140A and 140B via the network 130. A FHIR application is provided to the client devices 140A and 140B via a web interface 160 or an application interface 150. The FHIR server 110 and the client devices 140A and 140B may each be implemented in a computer system, in whole or in part, as described below with respect to FIG. 15. The client devices 140A and 140B may be referred to collectively as client devices 140 or generically as a client device 140.

A FHIR model on the client device 140 requests FHIR data from the FHIR server 110 and converts the received FHIR data to a data format usable by a UI platform. A UI module uses the converted data to present a user interface on a display device of the client device 140.

Any of the machines, databases, or devices shown in FIG. 1 may be implemented in a general-purpose computer modified (e.g., configured or programmed) by software to be a special-purpose computer to perform the functions described herein for that machine, database, or device. For example, a computer system able to implement any one or more of the methodologies described herein is discussed below with respect to FIG. 15. As used herein, a "database" is a data storage resource and may store data structured as a text file, a table, a spreadsheet, a relational database (e.g., an object-relational database), a triple store, a hierarchical data store, a document-oriented NoSQL database, a file store, or any suitable combination thereof. The database may be an in-memory database. Moreover, any two or more of the machines, databases, or devices illustrated in FIG. 1 may be combined into a single machine, database, or device, and the functions described herein for any single machine, database, or device may be subdivided among multiple machines, databases, or devices.

The FHIR server 110 and the client devices 140A-140B are connected by the network 130. The network 130 may be any network that enables communication between or among machines, databases, and devices. Accordingly, the network 130 may be a wired network, a wireless network (e.g., a mobile or cellular network), or any suitable combination thereof. The network 130 may include one or more portions that constitute a private network, a public network (e.g., the Internet), or any suitable combination thereof.

Figure 2:
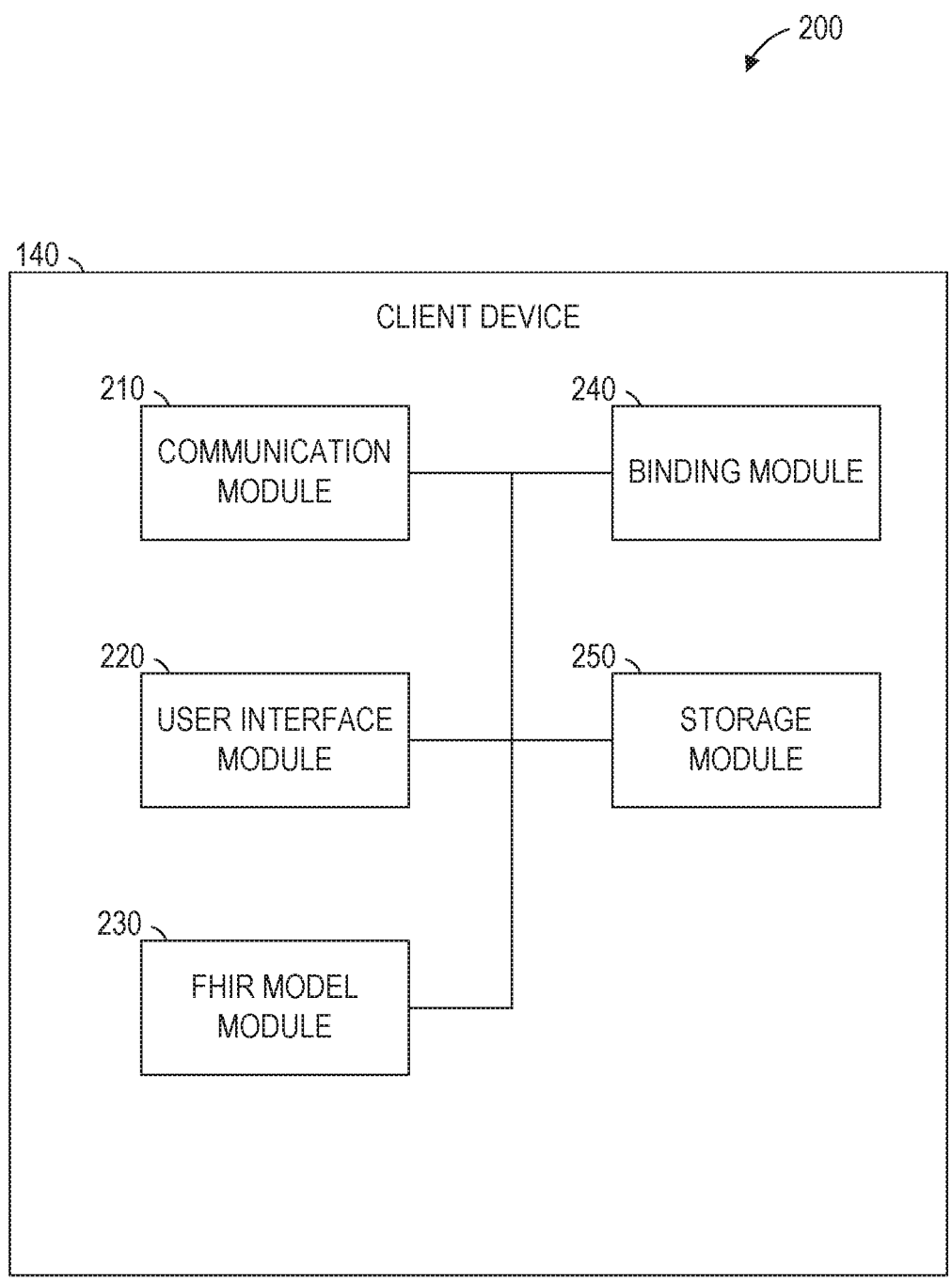
FIG. 2 is a block diagram of a client device, according to some example embodiments, suitable for using a FHIR model in presenting a user interface.

FIG. 2 is a block diagram 200 illustrating components of the client device 140, according to some example embodiments. The client device 140 is shown as including a communication module 210, a user interface module 220, a FHIR model module 230, a binding module 240, and a storage module 250, all configured to communicate with each other (e.g., via a bus, shared memory, or a switch). Any one or more of the modules described herein may be implemented using hardware (e.g., a processor of a machine). For example, any module described herein may be implemented by a processor configured to perform the operations described herein for that module. Moreover, any two or more of these modules may be combined into a single module, and the functions described herein for a single module may be subdivided among multiple modules. Furthermore, according to various example embodiments, modules described herein as being implemented within a single machine, database, or device may be distributed across multiple machines, databases, or devices.

The communication module 210 receives data sent to the client device 140 and transmits data from the client device 140. For example, the communication module 210 may receive, from the FHIR server 110, FHIR data for an application. The communication module 210 provides the data to the FHIR model module 230. The FHIR model module 230 communicates with the binding module 240 to bind the FHIR data to UI data structures. The UI data structures are provided to the user interface module 220, which generates a user interface based on the UI data structures.

In some example embodiments, data received via the user interface module 220 is converted to FHIR data by the FHIR model module 230 and provided to the FHIR server 110 using the communication module 210. The FHIR server 110 updates the FHIR data 120 in response. For example, the data may be stored in a database.

The user interface module 220 causes presentation of a user interface for the application server 110 on a display associated with the client device 140A or 140B. The user interface allows a user to view FHIR data, to modify FHIR data, to create new FHIR data, or any suitable combination thereof.

Figure 3:
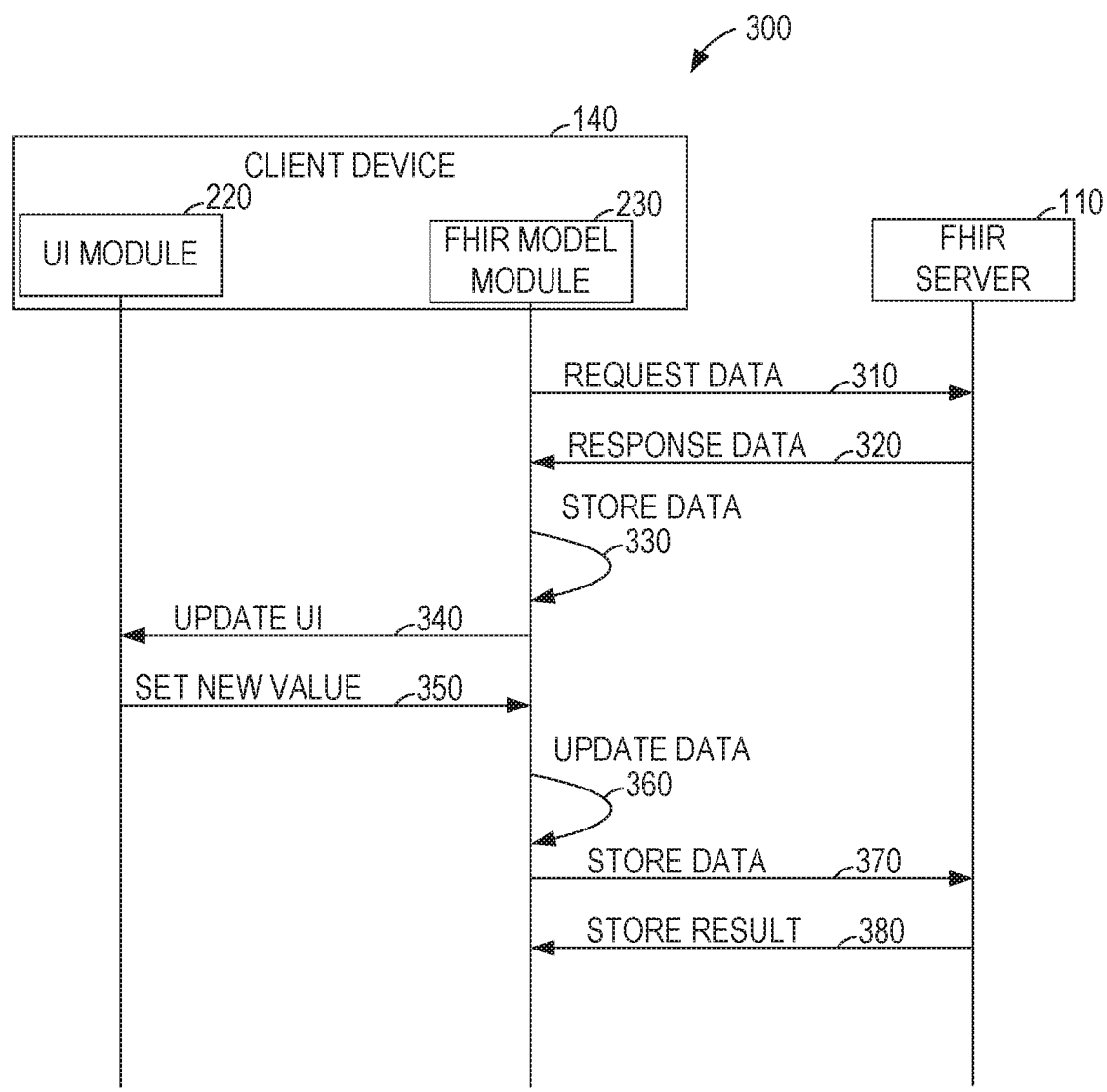
FIG. 3 is a flow diagram showing an example set of communications and operations in using a FHIR model in a user interface.

FIG. 3 is a flow diagram 300 showing an example set of communications and operations in using a FHIR model in a user interface. The flow diagram 300 shows communications 310, 320, 340, 350, 370, and 380 among the UI module 220 of the client device 140, the FHIR model module 230 of the client device 140, and the FHIR server 110. The flow diagram 300 also shows operations 330 and 360 of the FHIR model module 230.

In communication 310, the FHIR model module 230 requests FHIR data from the FHIR server 110. For example, an HTML or XML file may be parsed by the FHIR model module 230 to identify the FHIR server 110 and the FHIR data to request. The FHIR server 110 is identified by a FHIR service URL in the parsed file. In response to identifying the FHIR server 110 and the FHIR data to request, the FHIR model module 230 sends a request to the FHIR server 110 for the FHIR data via a network.

In communication 320, the FHIR server 110 responds to the communication 310 by sending responsive FHIR data. For example, if the request includes an identifier of an entity, the response includes data for the entity. The responsive FHIR data is in JavaScript object notation (JSON), XML, or resource description framework (RDF) format.

The FHIR model module 230, in operation 330, stores the received data on the client device 140. Thus, later uses of the same data in the HTML or XML file can be handled by retrieving the stored data instead of resending the request to the FHIR server 110.

In communication 340, the FHIR model module 230 causes the UI module 220 to update the UI with the received data. For example, data for the entity may be displayed on a screen of the client device 140.

Using the UI, a user may change a value of the displayed data (e.g., to change a name, an address, a current health condition, a relation between two entities, or any suitable combination thereof). The UI module 220, in communication 350, sets the new value with the FHIR model module 230.

In response to receiving the new value from the UI module 220, the FHIR model module 230 updates the data on the client device 140, in operation 360. Thus, later requests for the data from the FHIR model module 230 will be responded to with the new data.

In communication 370, the FHIR model module 230 sends the new value to the FHIR server 110. The FHIR server 110 updates the FHIR data 120 (of FIG. 1) to reflect the new value and sends communication 380 to acknowledge that the data was stored. If the data cannot be stored by the FHIR server 110, the communication 380 indicates that the attempt to store the data failed.

FIG. 4 is a block diagram of a database schema 400 suitable for storing FHIR data, according to some example embodiments. The database schema 400 includes a patient table 410, defined by a format 420 and including rows 430A, 430B, 430C, and 430D. Each of the rows 430A-430D includes a patient identifier, a name, a birthdate, and a name of an insurance provider for the patient. In some example embodiments, the FHIR model module 230 stores FHIR data in a JSON object store instead of in a relational database.

FIG. 5 is an example of portions of configuration files for a UI application suitable for using a FHIR model. Shown in FIG. 5 are registering code 510 and binding code 520.

The registering code 510 registers the uniform resource identifier (URI) of the FHIR server with the datasource name "fhir" and declares and initializes the FHIR model as using the "fhir" datasource.

The binding code 520 binds the page with identifier "MyPage" to the context of a patient with identifier 123 (e.g., the patient of row 430D of the patient table 410). The page displays two text fields, one with the name of the patient and one with the birthdate of the patient. The page also has a panel bound to a subcontext of the Patient 123 context, "animal."

A function, onInputChange, is defined that detects a change in value of a selector in the user interface and changes the binding of the page to the selected patient. Since the text fields are bound to the data fields of the patient, the UI application will automatically update the displayed data when the selected patient changes.

FIG. 6 is an example of an HTML file 600 suitable for providing a UI application using a FHIR model. The HTML file 600 creates a user interface using a UI platform for a "myhealthapp" component.

FIG. 7 is an example portion 700 of a configuration file for a UI application suitable for using a FHIR model. The portion 700 defines the "myhealthapp" component and may be stored in a "Component.js" file.

FIG. 8 is an example of an XML file suitable for providing a view of a UI application using a FHIR model. The XML file 800 defines a view for the "myhealthapp" component. The view shows two tiles, a first tile with data for patients and a second tile with data for organizations.

FIG. 9 is an example of a configuration file 900 suitable for providing a controller of a UI application using a FHIR model. The configuration file 900 may be a Home.controller.js file stored in a webapp/controller directory. The configuration file 900 defines a first function that responds to a press of the Patients tile and a second function that responds to a press of the Organizations tile. Thus, the configuration file 900 and the XML file 800 work in concert to create the UI application using the FHIR model.

FIG. 10 is an example of a configuration file 1000 suitable for configuring an application router for use with a UI application using a FHIR model. The configuration file 1000 may be an xs-app.json file stored in a localAppr directory. The configuration file 1000 defines routes between a FHIR server (e.g., the FHIR server 110) and local directories (e.g., directories on the client device 140A).

FIG. 11 is an example of portions 1110, 1120, and 1130 of a manifest file (e.g., a manifest.json file) for a UI application suitable for using a FHIR model. The portion 1110 defines a datasource of type "fhir" and may be added to a property to register the FHIR server (e.g., the FHIR server 110). The portion 1120 may be added to a property to allow the FHIR data to be accessed. The portion 1130 may be added to a property to declare and initialize a FHIR model.

FIG. 12 is an example of an XML file 1200 suitable for providing a view of a UI application using a FHIR model. The XML file 1200 may be stored as Home.view.xml. The controllerName element of the core tag identifies the controller associated with the view, in this case, the myhealthapp.controller.Home controller defined in the configuration file 900. The view includes two tiles: a first tile with a number of patients and a second tile with a number of organizations.

FIG. 13 is a block diagram of an example user interface 1300 generated using a FHIR model. The user interface 1300 includes a title 1310, descriptors 1320, 1330, and 1340, inputs 1350, 1360, and 1370, and a data region 1380. The title 1310 indicates that the user interface 1300 is for a patient search. Each of the descriptors 1320-1340 indicates the type of filter applied to a corresponding one of the inputs 1350-1370. The data region 1380 displays patient data responsive to the filters defined by the inputs 1350-1370.

The input 1350 accepts a date and may be implemented as a text field, a date picker, a drop-down list, a combo box, or another control type. As indicated by the descriptor 1320, the input 1350 is for a date of birth. In the example of FIG. 13, the date of birth is set to Feb. 17, 1983.

As indicated by the descriptor 1330, the input 1360 is for a patient's name. The input 1360 may be implemented as a text field, a drop-down list, a combo box, or another control type. The input 1370 is operable to indicate one or more insurance providers, as indicated by the descriptor 1340. The input 1370 may be implemented as a text field, a drop-down list, a combo box, or another control type.

As shown in FIG. 13, the only filter set is the date of birth. Accordingly, the data region 1380 displays records for patients born on Feb. 17, 1983 regardless of name or insurance provider.

Figure 14:
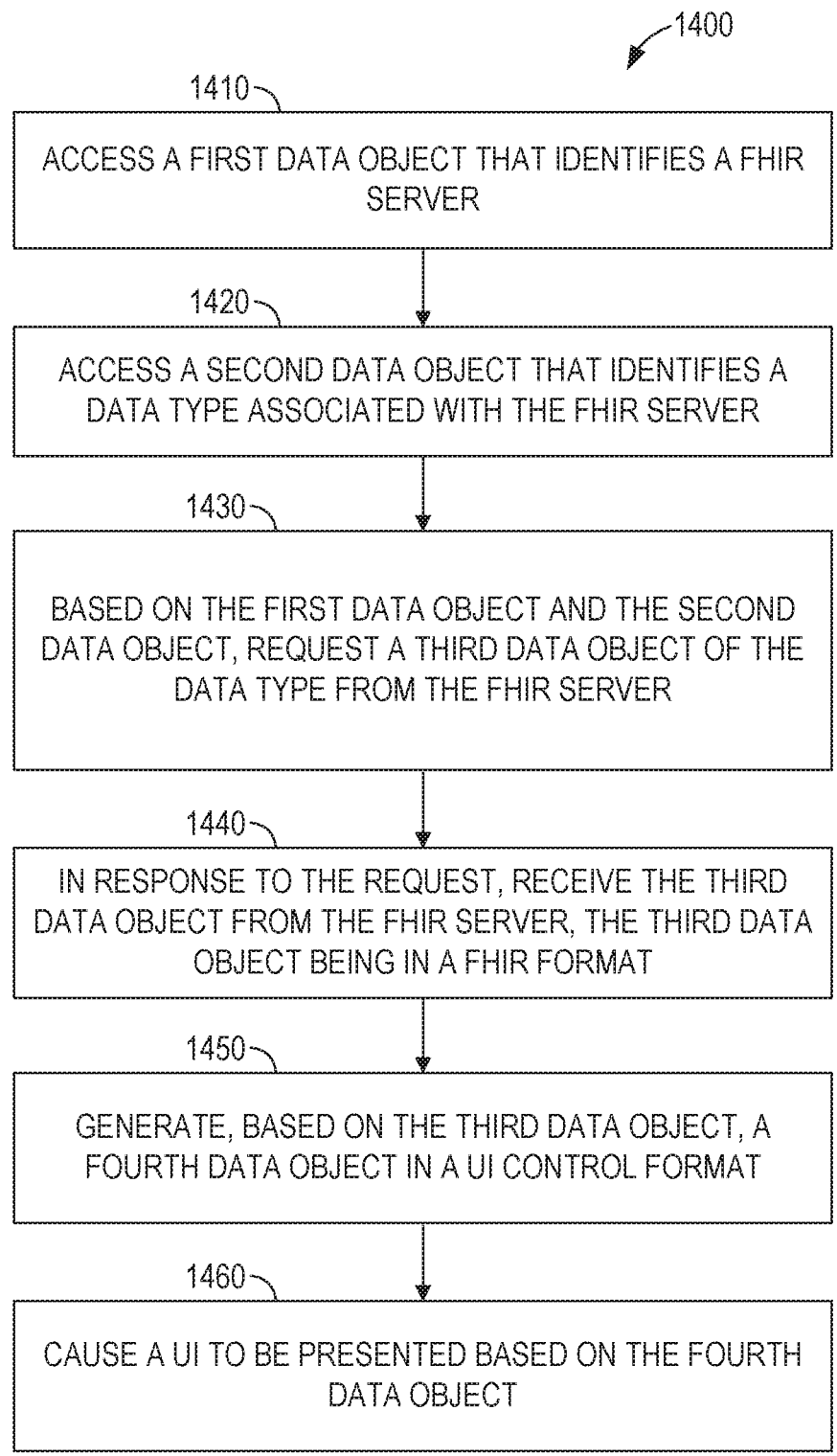
FIG. 14 is a flowchart illustrating operations of a method suitable for using a FHIR model to generate a user interface, according to some example embodiments.

FIG. 14 is a flowchart illustrating operations of a method 1400 suitable for using a FHIR model to generate a user interface, according to some example embodiments. The method 1400 includes operations 1410, 1420, 1430, 1440, 1450, and 1460. By way of example and not limitation, the method 1400 is described as being performed by the devices, modules, and databases of FIGS. 1-2.

In operation 1410, the FHIR model module 230 accesses a first data object that identifies a FHIR server (e.g., the FHIR server 110). For example, an environment variable may be accessed that includes a URL for the FHIR server. The environment variable may be set by execution of a batch file by the UI module 220. For example, a set_env.bat file may be located in a root folder of a UI application. The set_env.bat file may include a command to set the environment variable, e.g., "set destinations=[{"name": "fhirBackend", "url": http://test.fhir.org}]" to set the environment variable "fhirBackend" to the URL "http://test.fhir.org.".

As another example, a property in a manifest.json file of a UI application may identify the FHIR server as in the code 510 of FIG. 5.

In operation 1420, the FHIR model module 230 accesses a second data object that identifies a data type associated with the FHIR server. For example, an XML file may include, <GenericTile id="myPatientsTile" binding="{/Patient}">

In this example, the binding identifies the data type of "Patient" for the tile.

The data type may be a context data type, a property data type, a list data type, or another data type. Context binding binds UI elements to a specific object in FHIR model data. Binding elements to objects creates a binding context and enables relative binding within the control and all of its children. Using the binding property of a UI control binds a context to a control. For example, <Page id="myPage" binding="{/Patient/123}"> binds the page with identifier "myPage" to the Patient object with identifier 123 (e.g., the patient data stored in the row 330D of FIG. 3).

Property binding binds a specific property of a UI control to a specific property in the FHIR model data. For example, <Text id="myText" text="{/Patient/123/gender}"> binds the text field with identifier "myText" to the gender property of the Patient object with identifier 123.

List binding binds a list in a UI control to a list of properties in the FHIR model data. For example,

```
<List id="myList" items="{/Patient}">
  <StandardListItem title="{gender}" description="{birthdate}"/>
<List>
``` binds a list with identifier "myList" to the gender and birthdate properties of the Patient objects in the FHIR model data.

Based on the first data object and the second data object, the FHIR model module 230, in operation 1430, requests a third data object of the data type from the FHIR server. As an example, the FHIR model module 230 connects to the FHIR server 110 over the network 130 using the fhirBackend URL and sends a request for data of the type "Patient," data for a specific patient "Patient/123," or any suitable combination thereof.

In operation 1440, the FHIR model module 230 receives the third data object from the FHIR server, the third data object being in a FHIR format. The third data object contains a plurality of properties for the entity. An example of a FHIR-formatted data object for a patient is:

```
{
    "fullUrl": http://localhost:8080/fhir/Patient/123,
    "resource", {
        "resourceType": "Patient",
        "id": "123",
        "meta": {
            "versionId": "1"
        },
        "name": [{
            "family": "Schmoe",
            "given": [
                "Joe"
            ]
        }]
        "birthdate": [{
            "year": "1983",
            "month": "4",
            "day": "1"
        }],
        "insurance": {
            "provider": "United Health"
        }
    }
}
```

In operation 1450, the FHIR model module 230 generates, based on the received third data object, a fourth data object in a UI control format (e.g., in a UI control format as shown below).

```
<mvc:View xmlns:mvc="ui.core.mvc" xmlns="m"
controllerName="controller.fhir">
    <Page title="Patient Details">
        <content>
            <Label text="Family Name:"/>
            <Input value="{name/0/Family}"/>
            <Label text="Given Name:"/>
            <Input value="{name/0/Given}"/>
        </content>
    </Page>
</mvc:View>
```

The FHIR model module 230 may transform the structure of the third data object to generate the fourth data object. In some example embodiments, the third data object is in a flat data format and the fourth data object is in a tree data format. For example,

```
<Tree id="tree" items="{path: '/Organization', parameters: {rootsearch: 'partOf', rootProperty: 'id', rootValue: '1001', nodeProperty: 'id'}}">
    <StandardTreeItem title="{name}" />
</Tree>
``` defines a Tree user interface object with identifier "tree." The tree begins with the Organization with identifier 1001 and displays the name of each Organization in the tree. The FHIR model module 230 provides a tree data structure to the UI module 220 for display but receives flat data from the FHIR server 110. The data structure for each Organization includes a "partOf" attribute that contains the identifier of a parent Organization (or NULL if an Organization has no parent). Using this relationship data, the FHIR module 230 transforms the flat data of the third data object received in operation 1420 to generate the fourth data object in a tree data format. In this example embodiment, the "partOf" attribute is used to define the hierarchical relationship, but other attributes may be used.

The UI module 220, in operation 1460, causes a UI to be presented based on the fourth data object. For example, the user interface 400 may be presented, including the data received in the data region 1380.

In some example embodiments, the second data object identifies a field of the data type, the third data object comprises a value for the field, and the UI comprises a selector for the field, the selector having a default value set to the value. For example,

```
<Page binding="{/Patient/123}">
    <Select id="genderSelect" items="{gender}" selectedKey="{gender}" forceSelection="false">
        <core:Item key="{code}" text="{display}"/>
    </Select>
</Page>
``` binds the page to the Patient 123 and creates a selector with identifier "genderSelect." The items in the selector are the possible values of the gender field and the initially-selected value (or key) of the selector is the gender value for Patient 123. The items in the list have identifiers stored in the code attribute of the gender data type and are displayed using text stored in the display attribute of the gender data type.

In handling the "Select" construction, the FHIR model module 230 detects, based on the underlying StructureDefinition of the bound FHIR resource if there is a ValueSet configured for the property. If yes, the values in the ValueSet are used to populate the selector. Thus, if the values for gender are "Male" and "Female," the selector will populate with those two options.

In some example embodiments, the second data object identifies a number of records to retrieve and the request of operation 1430 requests the identified number of records. For example,

```
<List id="patientList" items="{/Patient}" growing="true"
growingThreshold="5">
    <StandardListItem title="{name/[use='official']/family" />
</List>
``` creates a list of official family names of Patients. The "growing" argument indicates that fewer than all Patients objects are initially requested. The "growingThreshold" argument indicates that only five objects are initially requested and additional objects will be requested five at a time (e.g., in response to a user scrolling to the end of the list).

There are use cases where the total number of resources should be displayed. Thus, in some example embodiments, the third data object comprises a count of records on the FHIR server. For example,

```
<GenericTile id="PatientsTile" binding="/Patient" header="My Patients">
    <TileContent unit="Patients">
        <NumericContent value="{%total%}" icon="icon://stethoscope"/>
    </Tile Content>
<GenericTile>
``` creates a tile with a binding to all Patients and a NumericContent UI element bound to the total number of Patients.

Though the method 1400 is described as generating a single object in the UI control format, operations 1420-1450 may be repeated for additional data objects using data from the FHIR server identified in operation 1410. In operation 1460, the presented UI is further based on the additional UI control data objects. For example, the UI 1300 is generated based on a context binding for the Patient resource type for the page, a list binding for the display area 1380, a context binding for the Insurance resource type for the input 1370, and so on.

To reduce the number of requests to the FHIR endpoint, the FHIR model module 230 supports bundled requests. When requests are bundled, data for multiple entities is requested from the FHIR endpoint in a single request. Requests are bundled as either a batch or a transaction. When processed as a batch, each request is independently handled by the FHIR endpoint. When processed as a transaction, if any request fails, the entire bundle is not performed at all. Unbundled bindings are referred to as direct bindings. In an example embodiment, a manifest.json file specifies which bundled bindings are handled as batches and which are handled as transactions. For example,

```
"models": {
    "": {
        "type": "health.model.fhir.FHIRModel",
        "dataSource": "local",
        "settings": {
            "groupProperties": {
                "A": {
                    "submit": "Batch"
                },
                "B": {
                    "submit": "Transaction"
                }
            }
        }
    }
}
``` defines two groups of bindings, "A" and "B." The requests for the "A" bindings will be handled as batches; requests for the "B" bindings will be handled as transactions.

The FHIR model module 230 recognizes that a binding is assigned to a binding by use of the "groupId" parameter in the binding declaration. For example,

```
<Panel id="myPatient" binding="{path: '/Patient/XYZ', parameters:
{groupId: 'A'}}">
    <Input value="{name/[use='official']/family}"/>
    <Input value="{name/[use='official']/given}"/>
    <Button text="Save" press="onSavePress"/>
</Panel>
<List items="{path: '/Patient', parameters: {groupId: 'A'}}">
    <StandardListItem title="{name/[use='official']/family},
{name/[use='official']/given}"/>
</List>
``` defines a panel bound to a Patient XYZ and a list of Patient names. Both bindings are part of group "A" and thus the requests for the data from the FHIR server will be bundled by the FHIR model module 230 into a batch.

Thus, by use of the method 1400, FHIR data is accessed and a UI is generated without requiring additional processing by an application. The application merely identifies the FHIR server, the FHIR data, and the manner in which the FHIR data should be included in the UI without needed to specify how the FHIR data is processed to generate the UI.

EXAMPLES

Example 1

A method comprising:

accessing, at a client device, a first data object that identifies a fast healthcare interoperability resources (FHIR) server;

accessing, at the client device, a second data object that identifies a data type associated with the FHIR server;

based on the first data object and the second data object, requesting, via a network, a third data object of the data type from the FHIR server;

in response to the request, receiving, at the client device and via the network, the third data object from the FHIR server, the third data object being in a FHIR format;

generating, at the client device and based on the third data object, a fourth data object in a user interface control format; and causing, by one or more hardware processors of the client device, a user interface to be presented based on the fourth data object.

Example 2

The method of example 1, wherein the second data object is in extensible markup language (XML) format.

Example 3

The method of examples 1 or example 2, wherein the data contains a plurality of properties for an entity.

Example 4

The method of examples 1 or example 2, wherein the data contains a plurality of properties for each of a list of entities.

Example 5

The method of examples 1 or example 2, wherein the third data object is in a flat data format and the fourth data object is in a tree data format.

Example 6

The method of any of examples 1 to 5, wherein:
the second data object identifies a field of the data type;
the third data object comprises a value for the field; and
the user interface comprises a selector for the field, the selector having a default value set to the value.

Example 7

The method of any of examples 1 to 6, wherein:
the second data object identifies a number of records to retrieve; and
the request requests the number of records.

Example 8

The method of any of examples 1 to 7, further comprising:
accessing, at the client device, a fifth data object that identifies a second data type associated with the FHIR server;
based on the first data object and the fifth data object, requesting, via a network, a sixth data object of the second data type from the FHIR server;
in response to the request for the sixth data object, receiving, at the client device and via the network, the sixth data object from the FHIR server, the sixth data object being in a FHIR format; and
generating, at the client device and based on the sixth data object, a seventh data object in the user interface control format; and wherein
the causing of the user interface to be presented further causes the user interface to be presented based on the seventh data object.

Example 9

The method of example 8, wherein the sixth data object comprises a count of records on the FHIR server.

Example 10

The method of any of examples 1 to 9, further comprising:
receiving, via the user interface, an updated value for the third data object;
providing, to the FHIR server via a network, the updated value for the third data object; and
receiving, from the FHIR server via the network, a confirmation that the third data object is updated to use the updated value.

Example 11

A system comprising:
a memory that stores instructions; and
one or more processors configured by the instructions to perform operations comprising:
accessing a first data object that identifies a fast healthcare interoperability resources (FHIR) server;
accessing a second data object that identifies a data type associated with the FHIR server;
based on the first data object and the second data object, requesting, via a network, a third data object of the data type from the FHIR server;
in response to the request, receiving, via the network, the third data object from the FHIR server, the third data object being in a FHIR format;
generating, based on the third data object, fourth data object in a user interface control format; and
causing a user interface to be presented based on the fourth data object.

Example 12

The system of example 11, wherein the second data object is in extensible markup language (XML) format.

Example 13

The system of example 11 or example 12, wherein the data contains a plurality of properties for an entity.

Example 14

The system of example 11 or example 12, wherein the data contains a plurality of properties for each of a list of entities.

Example 15

The system of any of examples 11 to 14, wherein the third data object is in a flat data format and the fourth data object is in a tree data format.

Example 16

A non-transitory computer-readable medium that stores instructions that, when executed by one or more processors, cause the one or more processors to perform operations comprising:
accessing a first data object that identifies a fast healthcare interoperability resources (FHIR) server;
accessing a second data object that identifies a data type associated with the FHIR server;
based on the first data object and the second data object, requesting, via a network, a third data object of the data type from the FHIR server;
in response to the request, receiving, via the network, the third data object from the FHIR server, the third data object being in a FHIR format;
generating, based on the third data object, a fourth data object in a user interface control format; and causing a user interface to be presented based on the fourth data object.

Example 17

The computer-readable medium of example 16, wherein the second data object is in extensible markup language (XML) format.

Example 18

The computer-readable medium of example 16 or example 17, wherein the data contains a plurality of properties for an entity.

Example 19

The computer-readable medium of example 16 or example 17, wherein the data type is a property data contains a plurality of properties for each of a list of entities.

Example 20

The computer-readable medium of example 16 or example 17, wherein the third data object is in a flat data format and the fourth data object is in a tree data format.

Figure 15:
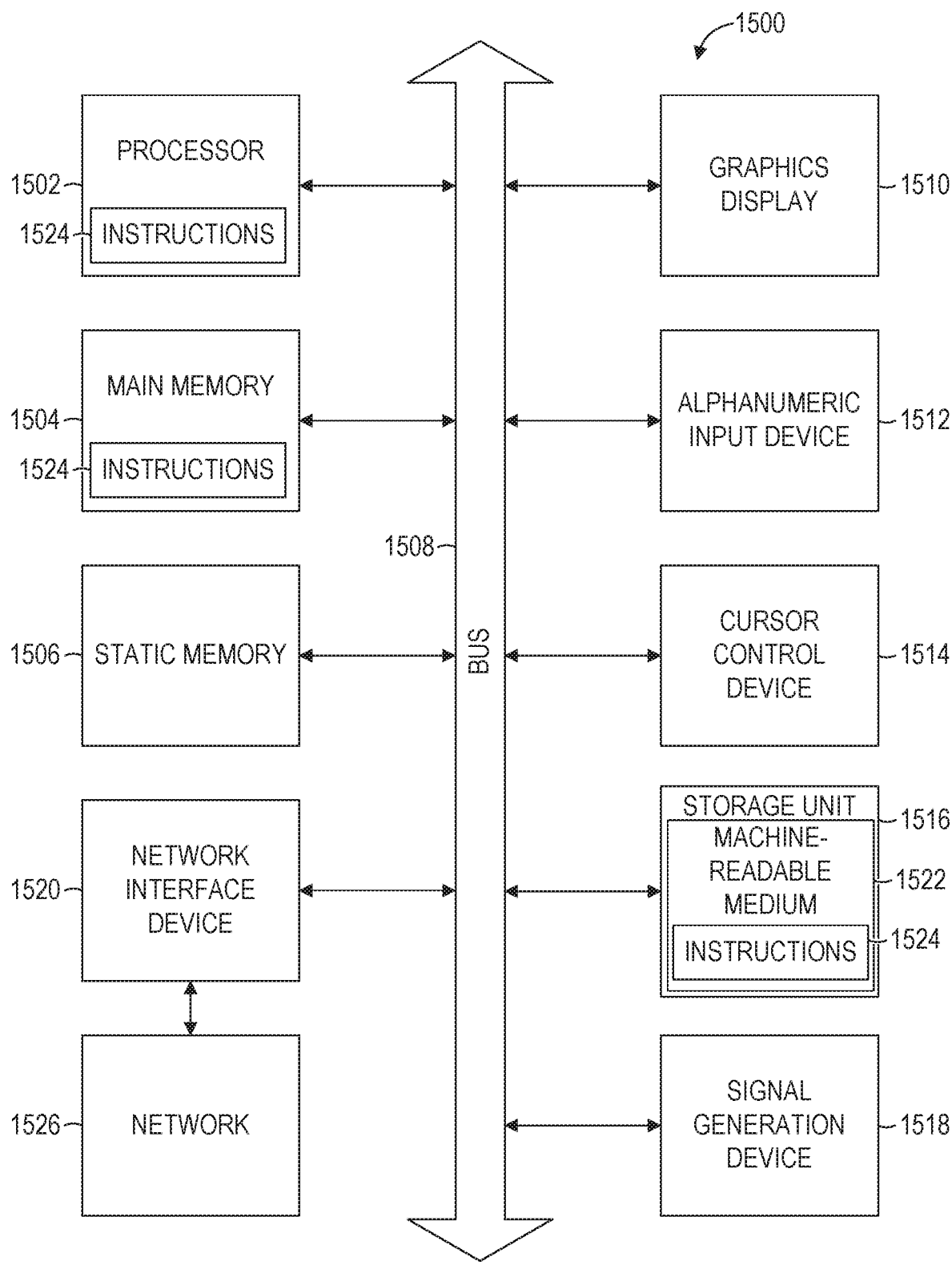
FIG. 15 is a block diagram illustrating components of a machine, according to some example embodiments.

FIG. 15 is a block diagram illustrating components of a machine 1500, according to some example embodiments, able to read instructions from a machine-readable medium (e.g., a machine-readable storage medium, a computer-readable storage medium, or any suitable combination thereof) and perform any one or more of the methodologies discussed herein, in whole or in part. Specifically, FIG. 15 shows a diagrammatic representation of the machine 1500 in the example form of a computer system within which instructions 1524 (e.g., software, a program, an application, an applet, an app, or other executable code) for causing the machine 1500 to perform any one or more of the methodologies discussed herein may be executed, in whole or in part. In alternative embodiments, the machine 1500 operates as a standalone device or may be connected (e.g., networked) to other machines. In a networked deployment, the machine 1500 may operate in the capacity of a server machine or a client machine in a server-client network environment, or as a peer machine in a distributed (e.g., peer-to-peer) network environment. The machine 1500 may be a server computer, a client computer, a personal computer (PC), a tablet computer, a laptop computer, a netbook, a set-top box (STB), a personal digital assistant (PDA), a cellular telephone, a smartphone, a web appliance, a network router, a network switch, a network bridge, or any machine capable of executing the instructions 1524, sequentially or otherwise, that specify actions to be taken by that machine. Further, while only a single machine is illustrated, the term "machine" shall also be taken to include a collection of machines that individually or jointly execute the instructions 1524 to perform all or part of any one or more of the methodologies discussed herein.

The machine 1500 includes a processor 1502 (e.g., a central processing unit (CPU), a graphics processing unit (GPU), a digital signal processor (DSP), an application-specific integrated circuit (ASIC), a radio-frequency integrated circuit (RFIC), or any suitable combination thereof), a main memory 1504, and a static memory 1506, which are configured to communicate with each other via a bus 1508. The machine 1500 may further include a graphics display 1510 (e.g., a plasma display panel (PDP), a light-emitting diode (LED) display, a liquid crystal display (LCD), a projector, or a cathode ray tube (CRT)). The machine 1500 may also include an alphanumeric input device 1512 (e.g., a keyboard), a cursor control device 1514 (e.g., a mouse, a touchpad, a trackball, a joystick, a motion sensor, or another pointing instrument), a storage unit 1516, a signal generation device 1518 (e.g., a speaker), and a network interface device 1520.

The storage unit 1516 includes a machine-readable medium 1522 on which are stored the instructions 1524 embodying any one or more of the methodologies or functions described herein. The instructions 1524 may also reside, completely or at least partially, within the main memory 1504, within the processor 1502 (e.g., within the processor's cache memory), or both, during execution thereof by the machine 1500. Accordingly, the main memory 1504 and the processor 1502 may be considered as machine-readable media. The instructions 1524 may be transmitted or received over a network 1526 via the network interface device 1520.

As used herein, the term "memory" refers to a machine-readable medium able to store data temporarily or permanently and may be taken to include, but not be limited to, random-access memory (RAM), read-only memory (ROM), buffer memory, flash memory, and cache memory. While the machine-readable medium 1522 is shown, in an example embodiment, to be a single medium, the term "machine-readable medium" should be taken to include a single medium or multiple media (e.g., a centralized or distributed database, or associated caches and servers) able to store instructions. The term "machine-readable medium" shall also be taken to include any medium, or combination of multiple media, that is capable of storing instructions for execution by a machine (e.g., the machine 1500), such that the instructions, when executed by one or more processors of the machine (e.g., the processor 1502), cause the machine to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" shall accordingly be taken to include, but not be limited to, one or more data repositories in the form of a solid-state memory, an optical medium, a magnetic medium, or any suitable combination thereof.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Certain embodiments are described herein as including logic or a number of components, modules, or mechanisms. Modules may constitute either software modules (e.g., code embodied on a machine-readable medium or in a transmission signal) or hardware modules. A "hardware module" is a tangible unit capable of performing certain operations and may be configured or arranged in a certain physical manner. In various example embodiments, one or more computer systems (e.g., a standalone computer system, a client computer system, or a server computer system) or one or more hardware modules of a computer system (e.g., a processor or a group of processors) may be configured by software (e.g., an application or application portion) as a hardware module that operates to perform certain operations as described herein.

In some embodiments, a hardware module may be implemented mechanically, electronically, or any suitable combination thereof. For example, a hardware module may include dedicated circuitry or logic that is permanently configured to perform certain operations. For example, a hardware module may be a special-purpose processor, such as a field-programmable gate array (FPGA) or an ASIC. A hardware module may also include programmable logic or circuitry that is temporarily configured by software to perform certain operations. For example, a hardware module may include software encompassed within a general-purpose processor or other programmable processor. It will be appreciated that the decision to implement a hardware module mechanically, in dedicated and permanently configured circuitry, or in temporarily configured circuitry (e.g., configured by software) may be driven by cost and time considerations.

Accordingly, the phrase "hardware module" should be understood to encompass a tangible entity, be that an entity that is physically constructed, permanently configured (e.g., hardwired), or temporarily configured (e.g., programmed) to operate in a certain manner or to perform certain operations described herein. As used herein, "hardware-implemented module" refers to a hardware module. Considering embodiments in which hardware modules are temporarily configured (e.g., programmed), each of the hardware modules need not be configured or instantiated at any one instant in time. For example, where a hardware module comprises a general-purpose processor configured by software to become a special-purpose processor, the general-purpose processor may be configured as respectively different special-purpose processors (e.g., comprising different hardware modules) at different times. Software may accordingly configure a processor, for example, to constitute a particular hardware module at one instant of time and to constitute a different hardware module at a different instant of time.

Hardware modules can provide information to, and receive information from, other hardware modules. Accordingly, the described hardware modules may be regarded as being communicatively coupled. Where multiple hardware modules exist contemporaneously, communications may be achieved through signal transmission (e.g., over appropriate circuits and buses) between or among two or more of the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions described herein. As used herein, "processor-implemented module" refers to a hardware module implemented using one or more processors.

Similarly, the methods described herein may be at least partially processor-implemented, a processor being an example of hardware. For example, at least some of the operations of a method may be performed by one or more processors or processor-implemented modules. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an application programming interface (API)).

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Some portions of the subject matter discussed herein may be presented in terms of algorithms or symbolic representations of operations on data stored as bits or binary digital signals within a machine memory (e.g., a computer memory). Such algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities. Typically, but not necessarily, such quantities may take the form of electrical, magnetic, or optical signals capable of being stored, accessed, transferred, combined, compared, or otherwise manipulated by a machine. It is convenient at times, principally for reasons of common usage, to refer to such signals using words such as "data," "content," "bits," "values," "elements," "symbols," "characters," "terms," "numbers," "numerals," or the like. These words, however, are merely convenient labels and are to be associated with appropriate physical quantities.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or any suitable combination thereof), registers, or other machine components that receive, store, transmit, or display information. Furthermore, unless specifically stated otherwise, the terms "a" and "an" are herein used, as is common in patent documents, to include one or more than one instance. Finally, as used herein, the conjunction "or" refers to a non-exclusive "or," unless specifically stated otherwise.

What is claimed is:

1. A method comprising:
accessing, at a client device, a first data object that identifies a fast healthcare interoperability resources (FHIR) server;
accessing, at the client device, a second data object that identifies a data type associated with the FHIR server;
based on the first data object and the second data object, requesting, via a network, a third data object of the data type from the FHIR server;
in response to the request, receiving, at the client device and via the network, the third data object from the FHIR server, the third data object being in a FHIR format;
generating, at the client device and based on the third data object, a fourth data object in a user interface control format; and
causing, by one or more hardware processors of the client device, a user interface to be presented based on the fourth data object.

2. The method of claim 1, wherein:
the second data object is in extensible markup language (XML) format; and
the second data object identifies a component of the user interface that is bound to the data type.

3. The method of claim 1, wherein the third data object contains a plurality of properties for an entity.

4. The method of claim 1, wherein the third data object contains a plurality of properties for each of a list of entities.

5. The method of claim 1, wherein the third data object is in a flat data format and the fourth data object is in a tree data format.

6. The method of claim 1, wherein:
the second data object identifies a field of the data type;
the third data object comprises a value for the field; and
the user interface comprises a selector having an initially-selected value for the field set to the value, the selector operable to change the value of the field.

7. The method of claim 6, further comprising:
receiving, via the selector, an updated value for the field of the third data object;
providing, to the FHIR server via the network, the updated value for the field of the third data object; and
receiving, from the FHIR server via the network, a confirmation that the third data object is updated to use the updated value.

8. The method of claim 1, wherein:
the second data object identifies a number of records to retrieve; and
the requesting of the third data object comprises requesting the number of records.

9. The method of claim 1, further comprising:
accessing, at the client device, a fifth data object that identifies a second data type associated with the FHIR server;
based on the first data object and the fifth data object, requesting, via the network, a sixth data object of the second data type from the FHIR server;
in response to the request for the sixth data object, receiving, at the client device and via the network, the sixth data object from the FHIR server, the sixth data object being in a second FHIR format; and
generating, at the client device and based on the sixth data object, a seventh data object in the user interface control format; and
wherein the causing of the user interface to be presented further causes the user interface to be presented based on the seventh data object.

10. The method of claim 9, wherein the sixth data object comprises a count of records on the FHIR server.

11. A system comprising:
a memory that stores instructions; and
one or more processors configured by the instructions to perform operations comprising:
accessing a first data object that identifies a fast healthcare interoperability resources (FHIR) server;
accessing a second data object that identifies a data type associated with the FHIR server;
based on the first data object and the second data object, requesting, via a network, a third data object of the data type from the FHIR server;
in response to the request, receiving, via the network, the third data object from the FHIR server, the third data object being in a FHIR format;
generating, based on the third data object, a fourth data object in a user interface control format; and
causing a user interface to be presented based on the fourth data object.

12. The system of claim 11, wherein:
the second data object is in extensible markup language (XML) format; and
the second data object identifies a component of the user interface that is bound to the data type.

13. The system of claim 11, wherein the third data object contains a plurality of properties for an entity.

14. The system of claim 11, wherein the third data object contains a plurality of properties for each of a list of entities.

15. The system of claim 14, wherein the third data object is in a flat data format and the fourth data object is in a tree data format.

16. A non-transitory computer-readable medium that stores instructions that, when executed by one or more processors, cause the one or more processors to perform operations comprising:
accessing a first data object that identifies a fast healthcare interoperability resources (FHIR) server;
accessing a second data object that identifies a data type associated with the FHIR server;
based on the first data object and the second data object, requesting, via a network, a third data object of the data type from the FHIR server;
in response to the request, receiving, via the network, the third data object from the FHIR server, the third data object being in a FHIR format;
generating, based on the third data object, a fourth data object in a user interface control format; and
causing a user interface to be presented based on the fourth data object.

17. The computer-readable medium of claim 16, wherein:
the second data object is in extensible markup language (XML) format; and
the second data object identifies a component of the user interface that is bound to the data type.

18. The computer-readable medium of claim 16, wherein the third data object contains a plurality of properties for an entity.

19. The computer-readable medium of claim 16, wherein the third data object contains a plurality of properties for each of a list of entities.

20. The computer-readable medium of claim 16, wherein the third data object is in a flat data format and the fourth data object is in a tree data format.

\* \* \* \* \*